United States Patent
McLucas

(10) Patent No.: US 7,422,581 B2
(45) Date of Patent: Sep. 9, 2008

(54) CATHETER WITH ANGLED TIP OF REDUCED DIAMETER

(76) Inventor: Bruce McLucas, 100 UCLA Medical Plaza, Suite 310, Los Angeles, CA (US) 90024

( * ) Notice: Subject to any disclaimer, the term of this patent is extended or adjusted under 35 U.S.C. 154(b) by 0 days.

(21) Appl. No.: 11/219,173

(22) Filed: Sep. 2, 2005

(65) Prior Publication Data

US 2007/0060909 A1    Mar. 15, 2007

(51) Int. Cl.
*A61M 25/00* (2006.01)
(52) U.S. Cl. .................................................. 604/523
(58) Field of Classification Search ......... 604/523–532, 604/533, 534–539
See application file for complete search history.

(56) References Cited

U.S. PATENT DOCUMENTS

| | | | |
|---|---|---|---|
| 4,747,840 A * | 5/1988 | Ladika et al. ............... | 604/532 |
| 4,935,017 A * | 6/1990 | Sylvanowicz ............... | 604/532 |
| 4,976,691 A | 12/1990 | Sahota | |
| 5,044,369 A * | 9/1991 | Sahota ........................ | 600/435 |
| 5,306,263 A * | 4/1994 | Voda ........................... | 604/532 |
| 5,401,258 A * | 3/1995 | Voda ........................... | 604/532 |
| 5,680,873 A | 10/1997 | Berg | |
| 6,408,214 B1 | 6/2002 | Williams | |
| 2005/0113801 A1 | 5/2005 | Gandras | |

* cited by examiner

*Primary Examiner*—Manuel A Mendez
(74) *Attorney, Agent, or Firm*—Seldon & Scillieri

(57) ABSTRACT

A catheter is disclosed comprising a first generally tubular body segment formed about a generally first longitudinally-extending axis and having an outer diameter of no more than approximately 5 fr; and a second generally tubular body segment formed about a second axis and having an outer diameter of no more than approximately 4 fr, the first and second axes intersecting at an acute angle. Preferably, the catheter additionally includes a third generally tubular body segment formed about a third axis and having an outer diameter of no more than approximately 4 fr, the third axis intersecting the second axis at a second acute angle. Preferably, the sum of the two intersection angles is approximately 90°. In addition, the intersection angle of the first and second axes is preferably in the range of approximately 30°.

13 Claims, 1 Drawing Sheet

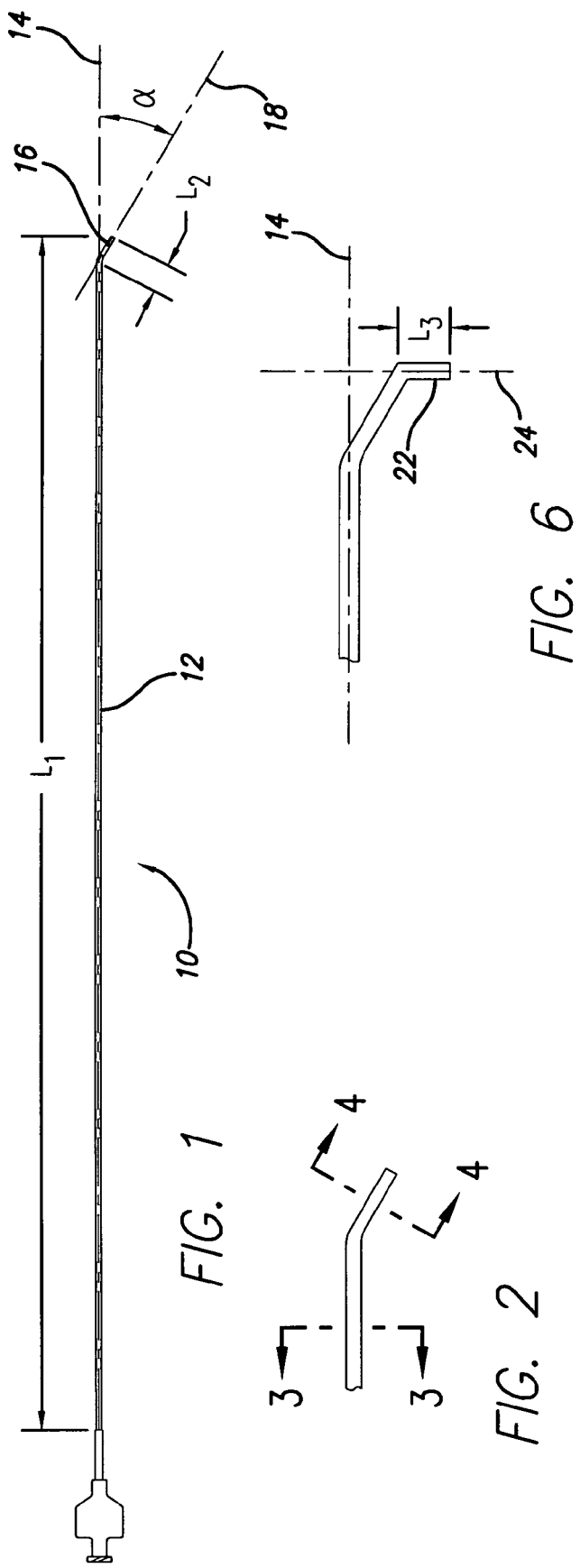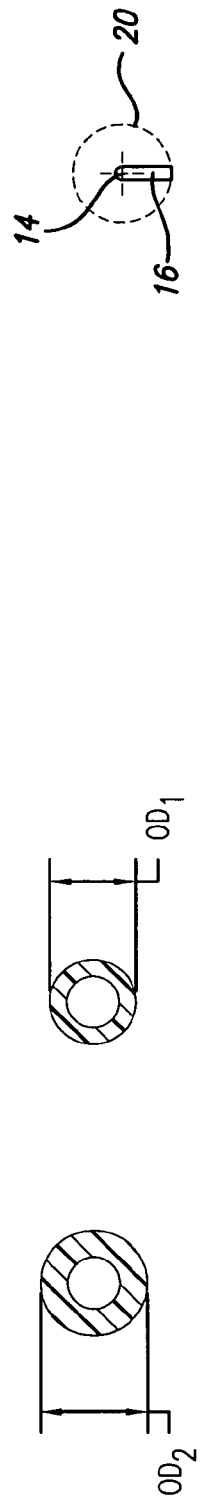

CATHETER WITH ANGLED TIP OF REDUCED DIAMETER

FIELD OF THE INVENTION

This invention relates to catheters such as angiographic catheters used in uterine artery embolization.

BACKGROUND OF THE INVENTION

Uterine artery embolization is directed to the removal of fibroids from the uterus. Fibroids are benign growths in the muscular wall of the uterus that can range in size from very small to quite large. Their known effects range from discomfort and backaches to interference with fertility.

There are many treatments available for women with fibroids. Medicine can shrink some fibroids, while surgery has been used in other cases. A relatively new way to treat women with fibroids is uterine fibroid embolization, which involves the cutting off of the fibroid's blood supply.

Fibroids require a supply of blood in order to grow, and will shrink or disappear completely when that supply is cut off. The embolization procedure entails the cutting of a tiny incision in the patient's groin region, and the passing of a small catheter through the patient's arterial system to the uterus. In practice, a radio-opaque catheter is fed into the femoral artery, while x-ray imaging is used to locate the relevant blood vessels and position the catheter. When the catheter has successfully navigated the arterial system to reach the targeted site, a fluid containing tiny particles is injected into the targeted area via the catheter. The particles, typically made of plastic or gelatin sponge, are about the size of grains of sand, and are moved by the pressure from the heart into the smaller arteries that are supplying blood to the fibroid. The particles become lodged in those arteries, and block blood flow to the fibroid. Over time, the fibroids consequently shrink or disappear.

In performing the embolization procedure, one must manipulate the catheter through a series of arteries and arterial branches of decreasing size in order to reach the targeted site. In accordance with well known techniques, the distal end of the catheter is inserted into the patient's femoral artery via the incision, and a thin, flexible, radio-opaque guide wire is advanced into and along the artery from the proximal end of the catheter. After advancing the wire for an appropriate distance, the catheter is advanced along the guide wire, the wire is further advanced, etc. Upon reaching a desired arterial branch, the wire is manipulated from the proximal end of the catheter so that its distal tip enters the desired branch and advances for some distance. The catheter is then advanced along the wire into and along the branch. This process is repeated until the desired site is reached.

Catheters must be sufficiently flexible to track the guide wire through sometimes tortuous paths, and must have an outer diameter that is sufficiently small to enter the arteries without causing damage. On the other hand, the catheters must be able to transmit the catheter-advancing longitudinally-directed force along the length of the catheter without kinking so that the catheter can be pushed through the patient's arterial system to reach the targeted area.

SUMMARY OF THE INVENTION

The invention herein is a catheter that enhances the physician's ability to manipulate the catheter and guide wire as the patient's arterial system is navigated. The catheter comprises (1) a first generally tubular body segment having proximal and distal ends, and formed with an outer diameter of no more than approximately 5 fr about a generally first longitudinally-extending axis, and (2) a second generally tubular body segment having a proximal end integrally coupled to the distal end of the first body segment, and a distal end, the second body segment being formed with an outer diameter of no more than approximately 4 fr about a second axis, the first and second axes intersecting at an acute intersection angle. (As used herein, the abbreviation "fr" refers to the unit of measurement of the "french scale" (also known as the "Charriere scale"). As known to those of ordinary skill in the art, the French scale is a scale for grading the sizes of catheters based on a measurement of ⅓ mm. Thus, for example, 3 fr=1 mm.) The subject catheter is accordingly inserted into the femoral artery with the second body segment preceding the first segment. As the catheter is advanced along an artery, it can be rotated about the first axis so that the consequential arc traversed by the distal end of the second body segment better orients the distal end of the guidewire for easier entry into desired arterial segments and branches and easier passage around curves in the path.

The catheter preferably includes a third generally tubular body segment integrally coupled to the distal end of the second body segment, and formed with an outer diameter of no more than approximately 4 fr about a third axis, the third axis intersecting the second axis at a second acute intersection angle. The catheter is inserted into the artery, with its third segment being inserted ahead of the second segment, to further enhance the ability of the physician to navigate through the arterial system by positioning the guide wire for very sharp turns owing to the additive nature of the two intersection angles.

Further details concerning the invention will be appreciated from the following detailed description of the invention, of which the drawing is a part.

THE DRAWING

In the drawing,

FIG. 1 is a side elevation view, in schematic, of a catheter constructed in accordance with the invention FIG. 2 is a magnified side elevation view of the distal portion of the catheter of FIG. 1 within the line 2-2 therein;

FIG. 3 is a is a cross-sectional view of the catheter of FIG. 1 taken along line 3-3 in FIG. 2;

FIG. 4 is a cross-sectional view of the catheter shown in FIG. 1 and taken along line 4-4 in FIG. 2;

FIG. 5 is a front elevation view of the catheter of FIG. 1, and

FIG. 6 is a side elevation view of a preferred modification to the distal portion of the catheter the right side of the catheter of FIG. 1.

DETAILED DESCRIPTION OF THE INVENTION

FIG. 1 is a side elevation view, in schematic, of a catheter constructed in accordance with the invention. A preferred catheter for use in uterine artery embolization will be described, although it will be recognized that other dimensions and angles may be used for some patients, some sites and/or other medical procedures. As illustrated in FIG. 1, and in cross-section in FIGS. 3-4, the catheter 10 comprises a first generally tubular body segment 12 formed about a generally first longitudinally-extending axis 14, and a second generally tubular body segment 16 formed about a second axis 18 and integrally coupled to the distal end of the first body segment. The preferred length $L_1$ of the catheter is approximately 45 cm. The preferred length $L_2$ of the second body segment is approximately 8.63 mm. The curved portion of the catheter transiting from the longitudinally-extending first segment to the acutely-extending second segment has a preferable radius of approximately 4.87 mm. The region within which the 5 fr outer diameter is reduced to 4 fr is not critical, within the dictates of human anatomy, and can occur on the curve or on either the proximal or distal sides of the curve.

Referring to FIGS. 3 and 4, the outer diameter $OD_1$ of the first body segment is no more than approximately 5 fr, and is preferably 5 fr. The outer diameter $OD_2$ of the second body segment is no more than approximately 4 fr, and is preferably 4 fr. The inner diameter of both segments is preferably approximately 0.97 mm. Referring to FIGS. 1 and 5, the first and second axes 14, 18 are generally coplanar and intersect at an acute angle α in the preferred range of approximately 30°-50°, and preferably at approximately 30°.

The distal end of the catheter 10, comprising the second body segment 16, is initially inserted through an incision in the patient's skin into the femoral artery. A thin flexible guide wire (not shown) having one or more radiographic markers is then inserted into the artery through the proximal end of the catheter so that it emerges form the distal end of the second segment body and is advanced some distance along the artery. The catheter is then advanced along the guide wire by a longitudinally-directed force exerted on the catheter segment exterior of the patient until the distal end of the catheter reaches the distal end region of the guide wire, whereupon the guide wire is again extended from the catheter by feeding an additional length of the guide wire into the catheter from the proximal end of the catheter and suitably rotating the guide wire about the first axis 14 as desired to traverse curves and branches in the arterial system in accordance with well known techniques and guide wire topography.

Owing to the oblique angle α of the second body segment 16, manipulation of the guide wire is facilitated with the subject invention. As the distal end of the catheter reaches a branch or curve that must be followed by the guide wire, the physician can appropriately rotate the catheter 10 about axis 14, causing the catheter's distal tip 22 to follow the circular path 20 illustrated in FIG. 5. This arcuate repositioning of the catheter's distal tip orients and positions the emerging guide wire's distal tip for easier entry into arterial branches and curves. After alternately advancing the wire and catheter in this manner to reach the desired site, the embolization process is performed, and the catheter removed from the patient.

Because the relatively longer proximal portion of the catheter is 5 fr, the catheter resists kinking as it travels long the relatively larger arteries that are initially encountered in the procedure. Because the second body segment is of a reduced 4 fr diameter, it is easily inserted into the smallest downstream artery that one expects to encounter in the procedure. Accordingly, a single catheter can be utilized to initially navigate the arterial system with the guide wire, and to thereafter deploy the embolizing fluid.

FIG. 6 is a side elevation view, n schematic, of a preferred modification to the distal end of the catheter shown in FIG. 1.

A third body segment 22, having a preferred length $L_3$ of approximately 5 mm, is formed about a third axis 24 that intersects the first body segment's axis 14 at a preferable angle of approximately 90°. Thus, if the angle α is approximately 30°, the axis 24 extends from the axis 18 at an angle of approximately 60°. The third body segment enhances the physician's ability to position and manipulate the entry of the catheter into downstream arteries by enhancing the ability to impose a downward force on the distal catheter tip.

Although the present invention and its advantages have been described in detail, it should be understood that various changes, substitutions and alterations can be made herein without departing from the spirit and scope of the invention as defined by the appended claims.

I claim:

1. A catheter comprising:
    a first generally tubular body segment formed about a first generally longitudinally-extending axis and having an outer diameter of no more than approximately 5 fr;
    a second generally tubular body segment formed about a second axis and having an outer diameter of no more than approximately 4 fr,
    the first and second axes being generally coplanar and intersecting at an acute angle.

2. The catheter of claim 1 including a third generally tubular body segment formed about a third axis and having an outer diameter of no more than approximately 4 fr, the third axis intersecting the second axis at an acute angle.

3. The catheter of claim 2 wherein the intersection of the first and second axes lie in approximately the same plane as the intersection of the second and third axes.

4. The catheter of claim 3 wherein the intersection angle of the first and second axes is in the range of approximately 25°-50°.

5. The catheter of claim 4 wherein the intersection angle of the second and third axes is in the range of approximately 40°-65°.

6. The catheter of claim 5 wherein the sum of the two intersection angles is approximately 90°.

7. The catheter of claim 3 wherein the intersection angle of the first and second axes is in the range of approximately 30°.

8. The catheter of claim 4 wherein the intersection angle of the second and third axes is approximately 60°.

9. The catheter of claim 2 where the longitudinal length of the catheter is in the range of 40-50 cm in length.

10. The catheter of claim 9 wherein the longitudinal length of the catheter is approximately 45 cm.

11. The catheter of claim 2 wherein the second body segment is in the range of approximately 5-11 mm in length.

12. The catheter of claim 11 wherein the second body segment is approximately 8.6 mm.

13. The catheter of claim 3 wherein the third body segment is in the range of approximately 5 mm.

* * * * *